United States Patent
O'Lenick, Jr.

(12) 
(10) Patent No.: US 6,878,682 B1
(45) Date of Patent: Apr. 12, 2005

(54) CAPPED NONIONIC SURFACTANTS

(75) Inventor: Anthony J. O'Lenick, Jr., Dacula, GA (US)

(73) Assignee: Colonial Chemical Inc., South Pittsburg, TN (US)

(*) Notice: Subject to any disclaimer, the term of this patent is extended or adjusted under 35 U.S.C. 154(b) by 123 days.

(21) Appl. No.: 10/443,173

(22) Filed: May 23, 2003

(51) Int. Cl.[7] .............................. C11D 1/72; C11D 3/37

(52) U.S. Cl. ..................... 510/356; 510/360; 510/421; 510/475; 568/579; 568/606; 568/616

(58) Field of Search ................................. 510/356, 360, 510/421, 475; 568/579, 606, 616

(56) References Cited

U.S. PATENT DOCUMENTS 4,780,237 A   10/1988   Schmid et al.

FOREIGN PATENT DOCUMENTS

| EP | 798320 | * 10/1997 | ......... C08F/222/00 |
| JP | 64-43513 | * 2/1989 | ......... C08F/222/40 |
| JP | 2-188545 | * 7/1990 | ............ C07C/43/17 |

* cited by examiner

*Primary Examiner*—Brian P. Mruk

(57) ABSTRACT

The invention relates to a series low foaming capped nonionic surfactants. These compounds by virtue of reacting the terminal hydroxyl group with methallyl chloride, have increased stability in alkali, lower high cloud points and can be reacted via free radical technology into polymer backbones, resulting in non-water blush surfactants.

15 Claims, No Drawings

CAPPED NONIONIC SURFACTANTS

FIELD OF THE INVENTION

The field of the invention relates to low foaming non-ionic surfactants. More specifically, the field is capped non-ionic surfactants. These compounds by virtue of reacting the terminal hydroxyl group with methallyl chloride, have increased stability in alkali, lower high cloud points and can be reacted via free radical technology into polymer backbones, resulting in non-water blush surfactants.

BACKGROUND OF THE INVENTION

Non-ionic surfactants have been known for many years. They are products used for detergency in many industrial applications. Non-ionic surfactants can be represented by the following structure:

$$R\text{—}O\text{—}(CH_2CH_2O)_x\text{—}H$$

wherein x is generally 3–10 and R is generally C12 alkyl.

These materials are good detergents, but also result in copious foam during processing. In many applications areas, foam is undesirable, causing problems with process equipment. To add to the problem, many industrial processes are run at very high pH values. A condition, which improves cleaning and degreasing, but in many cases destroys the non-ionic.

Non-ionic surfactants of this type have what is referred to as a high cloud point.

Specifically, when one heats up a clear solution of the non-ionic, the solution becomes cloudy. This is attributed to the inability of the polyoxyalkylene group ($-(CH_2CH_2O)_x-$) to hydrogen bind water. Once the high cloud point is reached, the ability to foam is destroyed, but detergency remains. Using a non-ionic at temperatures in excess of the cloud point of the non-ionic is one approach to controlling foam while still providing detergency. This approach does nothing to improve the alkaline stability of the molecule, since the chemical nature of the molecule itself has not been altered.

Additionally, the molecule may be modified to include polyoxypropylene groups onto the backbone.

$$R\text{—}O\text{—}(CH_2CH_2O)_x\text{—}(CH_2CH(CH_3)O)_y H$$

wherein x is generally 3–10 and R is generally C12 alkyl and y ranges from 2 to 5. This alteration provides improvement to the alkali stability, but only marginally.

Additional capping techniques have also been used. One approach is reaction with benzyl chloride resulting in the following structure;

$$R\text{—}O\text{—}(CH_2CH_2O)_x\text{—}CH_2\text{—}C_6H_5$$

wherein $C_6H_5$ is benzyl. These compounds are good for alkali stability, however they contain aromatic groups, which are generally undesirable. Additionally these products are expensive to make.

Another approach is to use thionyl chloride to produce chloride capped non-ionic surfactants. This results in the following product;

$$R\text{—}(OCH_2CH_2)_x Cl$$

These materials have the best alkali stability, but are very expensive due to the expense and special requirements of reacting the thionyl chloride.

Non-ionic surfactants are used not only to provide detergency, but also to provide emulsification. One area in which this is important is emulsion polymerization. If standard non-ionic compounds are used to make the emulsion in which the polymerization occurs, they can provide a phenomenon called water blush. Anyone who has spilled water on inexpensive vinyl has seen a white deposit form. This deposit is the result of a blooming to the surface of the emulsifier. If one is able to provide a vinyl reactive group to the emulsifier, the emulsifier will become attached to the polymer and be unable to blush to the surface. Therefore, another aspect of the present invention is to provide vinyl capping non-ionic surfactants that will react with the polymer matrix in the emulsion polymerization reaction, providing polymers that do not water blush.

None of the compounds known to date provide the compounds of the present invention. These unique materials provide lower foam, alkali stability, and non-blush attributes, while being very efficient detergents and emulsifiers.

SUMMARY OF THE INVENTION

The present invention relates to the reaction product of methallyl chloride (also called 3-chloro,-2-methyl-1-propene) with a nonionic surfactant. The reaction is as follows;

$$CH_2\!\!=\!\!C(CH_3)CH_2\text{—}Cl \;+$$
$$R\text{—}O\text{—}(CH_2CH_2O)_x\text{—}(CH_2CH(CH_3)O)_y H \xrightarrow{KOH}$$
$$R\text{—}O\text{—}(CH_2CH_2O)_x\text{—}(CH_2CH(CH_3)O)_y\text{—}CH_2\text{—}C(CH_3)\!\!=\!\!CH_2 \; KCl$$

DETAILED DESCRIPTION OF THE INVENTION

The present invention relates to a series of compounds conforming to the following structure:

$$R\text{—}O\text{—}(CH_2CH_2O)_x\text{—}(CH_2CH(CH_3)O)_y\text{—}CH_2\text{—}C(CH_3)\!\!=\!\!CH_2$$

wherein;

R is alkyl having 10 to 20 carbon atoms;
x is an integer ranging from 3 to 20;
y is an integer ranging from 0 to 20.
Preferred Embodiments
In a preferred embodiment R is C10.
In a preferred embodiment R is C12.
In a preferred embodiment R is C14.
In a preferred embodiment R is C16.
In a preferred embodiment R is C18.
In a preferred embodiment R is C20.
In a preferred embodiment y is 0.
In a preferred embodiment y ranges from 1 to 5.
In a preferred embodiment y ranges from 2 to 10.
In a preferred embodiment y ranges from 10 to 15.
In a preferred embodiment x ranges from 5 to 20.
In a preferred embodiment x ranges from 5–10.
In a preferred embodiment x ranges from 6–9.
In a preferred embodiment x ranges from 10–15.

EXAMPLES

Raw Materials

Methallyl Chloride

Methallyl chloride is also called 3-chloro,-2-methyl-1-propene. It is commercially available from FMC Corporation. It conforms to the following structure:

$CH_2\!=\!C(CH_3)CH_2Cl.$

Nonionic Surfactants

Nonionic surfactants suitable for the practice of the present invention are commercially available from a variety of source including Ethox in Greenville S.C. They conform to the following structure:

$R\!-\!O\!-\!(CH_2CH_2O)_x\!-\!(CH_2CH(CH_3)O)_yH$ wherein;
R is alkyl having 10 to 20 carbon atoms;
x is an integer ranging from 3 to 20;
y is an integer ranging from 0 to 20

Examples 1–10

| Example | R | X | Y |
|---|---|---|---|
| 1 | $C_{10}H_{21}$ | 3 | 0 |
| 2 | $C_{12}H_{25}$ | 9 | 3 |
| 3 | $C_{14}H_{29}$ | 10 | 0 |
| 4 | $C_{16}H_{33}$ | 10 | 5 |
| 5 | $C_{18}H_{37}$ | 15 | 0 |
| 6 | $C_{20}H_{41}$ | 20 | 10 |
| 7 | $C_{12}H_{25}$ | 10 | 10 |
| 8 | $C_{12}H_{25}$ | 5 | 15 |
| 9 | $C_{12}H_{25}$ | 6 | 0 |
| 10 | $C_{12}H_{25}$ | 20 | 20 |

General Reaction Procedure

The process for preparation of the compounds of the present invention is the Williamson Synthesis. In this reaction the non-ionic surfactant, the methallyl chloride and potassium hydroxide are added to a vessel and heated to 70–90° C., for 5–8 hours. During the reaction KCl is formed and in insoluble. It is removed via filtration and the desired products achieved. The product can be used as is or diluted with water.

Examples 10–20

The to 90.5 grams of methallyl chloride is added the specified number of grams of the specified nonionic and 56.1 grams of potassium hydroxide. The reaction mixture is heated to 75–85° C. and held 8 hours. During this time solid KCl is formed. After the reaction is complete the KCl is filtered off. The product conforms to the following structure:

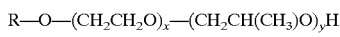

$R\!-\!O\!-\!(CH_2CH_2O)_x\!-\!(CH_2CH(CH_3)O)_y\!-\!\underset{\underset{CH_3}{|}}{C}H\!=\!CH_2$

|  | Nonionic Surfactant | |
|---|---|---|
| Example | Example | Grams |
| 11 | 1 | 260.0 |
| 12 | 2 | 682.0 |
| 13 | 3 | 717.0 |
| 14 | 4 | 613.0 |
| 15 | 5 | 836.0 |
| 16 | 6 | 2075.0 |
| 17 | 7 | 1093.0 |
| 18 | 8 | 1161.0 |
| 19 | 9 | 404.0 |
| 20 | 10 | 1625.0 |

Applications Examples

The products of the present invention are low foaming, alkali stable detergents that can be reacted into polymers by reaction of the terminal vinyl group with vinyl containing monomers like vinyl chloride.

Cloud Point

This test is performed on samples, which are in a liquid form. Prepare a 1% aqueous solution of the test material. Stir the cooling sample with a thermometer at a rate sufficient to keep the temperature throughout the sample uniform. When the sample has reached a temperature, which is about 10° C. above the expected cloud point, begin stirring steadily and rapidly in a circular motion so as to prevent super cooling and solidification of fat crystals on the sides or bottom of the bottle. Remove the bottle from the bath and inspect regularly. The cloud point is that temperature at which the immersed portion of the thermometer is no longer visible when viewed horizontally through the bottle and sample. Report the cloud point to the nearest degree Celsius.

| Product | Cloud Point 1% Sol |
|---|---|
| Starting Non-ionic (example 9) | 49.0° C. |
| Product of this invention (Example 19) | 21.6° C. |

Foam

The foam is measured using a 1% solution of surfactant in a graduated cylinder. 100 grams of the solution are added to a 500 ml graduated cylinder and shaken 5 times. The original foam and the foam in 60 seconds are measured.

| Product | Initial Foam | 60 Sec Foam |
|---|---|---|
| Starting Non-ionic (example 9) | 250 ml | 250 ml |
| Product of this invention (Example 19) | 70 ml | 60 ml |

Caustic Stability

The alkaline stability is measured by adding 3 grams of the non-ionic tested to 0.6 grams of solid KOH. The resulting mixture is held 1 hour at 110° C. discoloration is the monitored.

| Product | Appearance | Result |
| --- | --- | --- |
| Starting Non-ionic (example 9) | Discolored | Fail |
| Product of this invention (Example 19) | No Discoloration | Pass |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A non-ionic compound conforming to the following structure:

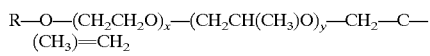

R—O—(CH$_2$CH$_2$O)$_x$—(CH$_2$CH(CH$_3$)O)$_y$—CH$_2$—C—(CH$_3$)=CH$_2$ wherein:

R is alkyl having 10 to 20 carbon atoms;

x is an integer ranging from 3 to 20;

y is an integer ranging from 0 to 20.

2. A non-ionic compound of claim 1 wherein R is C10.

3. A non-ionic compound of claim 1 wherein R is C12.

4. A non-ionic compound of claim 1 wherein R is C14.

5. A non-ionic compound of claim 1 wherein R is C16.

6. A non-ionic compound of claim 1 wherein R is C18.

7. A non-ionic compound of claim 1 wherein R is C20.

8. A non-ionic compound of claim 1 wherein y is 0.

9. A non-ionic compound of claim 1 wherein y ranges from 1 to 5.

10. A non-ionic compound of claim 1 wherein y ranges from 2 to 10.

11. A non-ionic compound of claim 1 wherein y ranges from 10 to 15.

12. A non-ionic compound of claim 1 wherein x ranges from 5 to 20.

13. A non-ionic compound of claim 1 wherein x ranges from 5 to 10.

14. A non-ionic compound of claim 1 wherein x ranges from 6 to 9.

15. A non-ionic compound of claim 1 wherein x ranges from 10 to 15.

* * * * *